United States Patent [19]

Matsen, III et al.

[11] Patent Number: 5,030,219
[45] Date of Patent: Jul. 9, 1991

[54] GLENOID COMPONENT INSTALLATION TOOLS

[75] Inventors: Frederick A. Matsen, III, Seattle, Wash.; John A. Engelhardt, Warsaw, Ind.; Jeffrey M. Ondrla, both of Warsaw, Ind.

[73] Assignee: Boehringer Mannheim Corporation, Indianapolis, Ind.

[21] Appl. No.: 468,266

[22] Filed: Jan. 22, 1990

[51] Int. Cl.$^5$ ................................................. A61F 5/04
[52] U.S. Cl. ..................................... 606/53; 606/80; 606/86; 606/96
[58] Field of Search ............... 623/16, 18, 19; 606/53, 606/54, 59, 60, 72, 73, 79, 80, 86, 96, 99, 102, 104

[56] References Cited

U.S. PATENT DOCUMENTS

| | | | |
|---|---|---|---|
| 4,528,980 | 7/1985 | Kenna | 606/80 |
| 4,712,951 | 12/1987 | Brown | 408/158 |
| 4,834,080 | 5/1989 | Brown | 606/96 |
| 4,865,605 | 9/1989 | Dines et al. | |
| 4,964,865 | 10/1990 | Burkhead et al. | 623/19 |

FOREIGN PATENT DOCUMENTS 0281763 9/1988 Fed. Rep. of Germany .
1091-920 5/1984 U.S.S.R. .

OTHER PUBLICATIONS

"The Cofield Total Shoulder System", 1989, by Richards Medical Company.

Primary Examiner—Stephen C. Pellegrino
Assistant Examiner—Steven J. Shumaker
Attorney, Agent, or Firm—Barnes & Thornburg

[57] ABSTRACT

The present invention relates to instruments for preparing a glenoid surface of a scapula to receive a prosthetic glenoid component to replace the natural socket of a shoulder. More particularly, the present invention relates to a drill guide assembly for aligning and guiding a drill bit to form holes in the glenoid surface at predetermined locations to secure the glenoid component to the glenoid surface. A reamer assembly including a ratchet drive mechanism is also included to facilitate preparation of the glenoid surface prior to installation of the glenoid component.

30 Claims, 3 Drawing Sheets

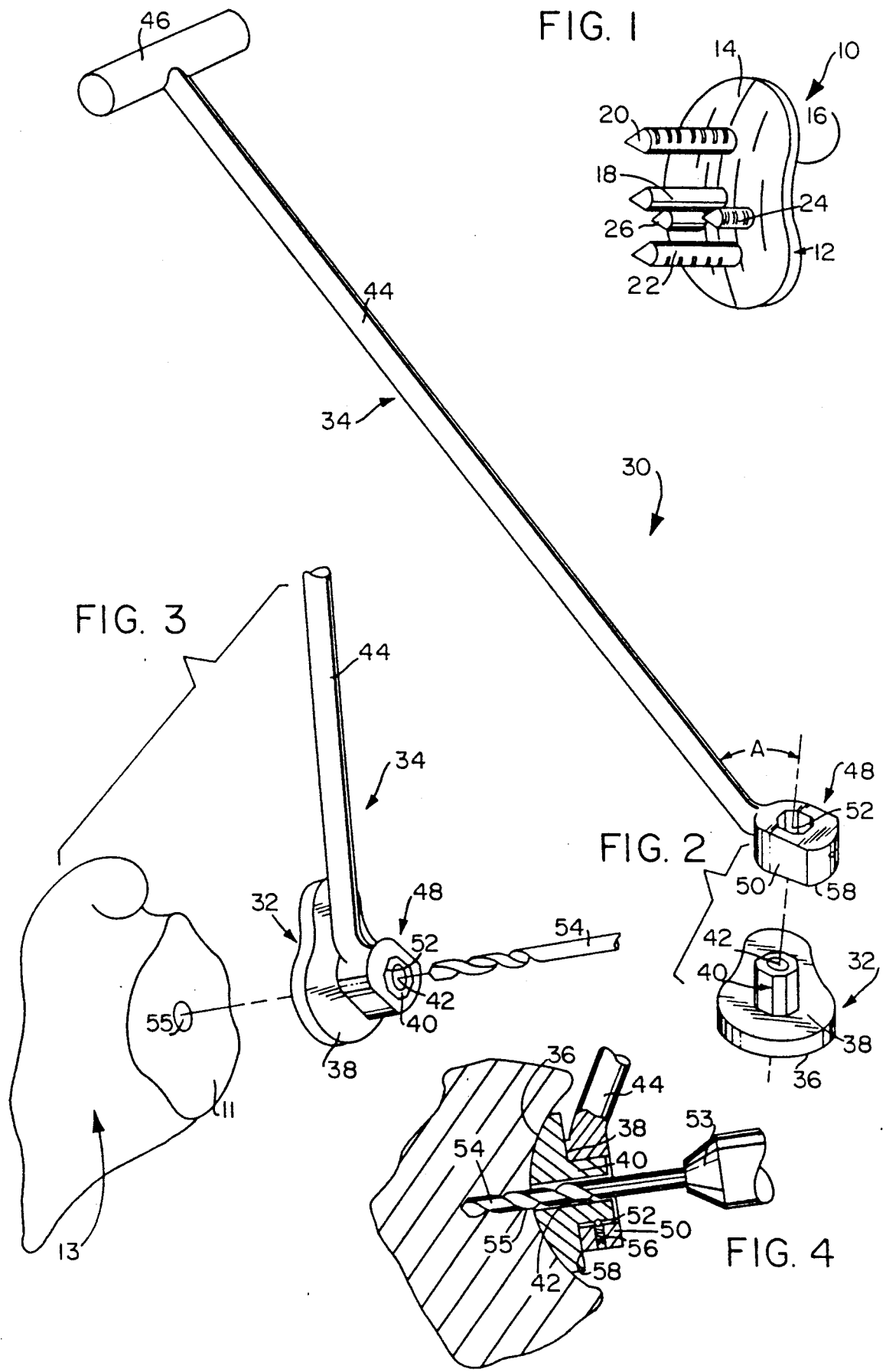

GLENOID COMPONENT INSTALLATION TOOLS

BACKGROUND AND SUMMARY OF THE INVENTION

The present invention relates to instruments for preparing a glenoid surface of a scapula to receive a prosthetic glenoid component to replace the natural socket of a shoulder. More particularly, the present invention relates to a drill guide assembly for aligning and guiding a drill bit to form holes in the glenoid surface at predetermined locations to receive attachment pegs formed on the glenoid component to secure the glenoid component to the glenoid surface. A reamer assembly including a ratchet drive mechanism is also included to facilitate preparation of the glenoid surface prior to installation of the glenoid component.

The instruments of the present invention are designed for use during a total shoulder replacement procedure. In a total shoulder replacement procedure, a humeral component having a head portion is used to replace the natural head portion of the arm bone or humerus. The humeral component typically has an elongated intramedullary stem to secure the humeral component to the humerus. The glenoid portion of the scapula is resurfaced with a glenoid component which provides a bearing surface for the head portion of the humeral component.

In order to install the glenoid component to the glenoid surface, it is necessary to drill holes in the glenoid surface for receiving attachment pegs formed on the glenoid component used to secure the glenoid component to the glenoid surface. It is known to use a drill guide to guide a drill bit to form holes in the glenoid surface at predetermined locations.

During the installation of glenoid components, it is often difficult to access the glenoid surface through the surgical incision. The precise angle at which the surgeon must approach the glenoid surface can vary with each operation. The surgeon typically has very little room to maneuver the instruments used to prepare the glenoid surface for receiving the glenoid component. Because installation of the glenoid component requires accurate positioning of the instruments on the glenoid surfaces, the limited access to the glenoid surface during the operation can cause problems.

Prior art drill guides include a rigidly attached handle aligned in only one orientation with respect to the drill guide Therefore, the glenoid surface can be approached from only one angle which is controlled by the angle that the handle is attached to the drill guide. Prior art drill guides require two separate drill guides having the handles mounted in different positions for use on the right and left side glenoid surfaces.

Prior art reamers are either hand held or designed to be attached to a drill for reaming the surface of a bone to prepare the surface for receiving prosthetic components. Because of the limited space available for accessing the glenoid surface, it is difficult to properly position a reamer on the glenoid surface to smooth and prepare the glenoid surface for receiving a glenoid component.

One object of the present invention is to provide a drill guide having an adjustable handle to facilitate positioning of the drill guide on the glenoid surface.

Another object of the present invention is to provide a ratchet mechanism for driving a reamer assembly to permit rotation of a reamer against the glenoid surface to prepare the glenoid surface for installation of a glenoid component despite the limited access available during a shoulder replacement procedure.

Yet another object of the present invention is to provide a mechanism for accurately aligning and guiding a drill bit to form a plurality of holes in a glenoid surface at predetermined locations for receiving a plurality of attachment pegs attached to a glenoid component to secure the glenoid component to the glenoid surface.

According to the present invention, an assembly is provided for aligning and guiding a drill bit to form a hole in a glenoid surface of a scapula at a predetermined location. The assembly includes a drill guide having a first surface for abutting the glenoid surface and an opposite outwardly facing second surface. The drill guide is formed to include an aperture extending between the first and second surfaces for guiding the drill bit to form a center hole in the glenoid surface. The assembly includes a handle for positioning the drill guide on the glenoid surface to align the aperture at the predetermined location over the glenoid surface. The assembly also includes means for coupling the handle to the drill guide in a selected one of the plurality of orientations to align the handle at a selected angle with respect to the drill guide to facilitate positioning of the drill guide on the glenoid surface.

In a preferred embodiment of the present invention, the drill guide includes a projection extending outwardly from the second surface. The coupling means includes a head portion attached to the handle for engaging the projection to align the handle in the selected orientation with respect to the drill guide.

In another preferred embodiment of the present invention, the drill guide includes alignment means coupled to the drill guide for engaging a portion of the glenoid to align the drill guide aperture in its predetermined location over the glenoid surface. The alignment means includes an L-shaped armed having a first leg coupled to the drill guide and a second leg for engaging the glenoid to align the drill guide aperture in its predetermined location and to stabilize the drill guide while drilling the hole.

In yet another preferred embodiment of the present invention, the drill guide includes a plurality of apertures for guiding the drill bit to form a plurality of holes in the glenoid surface in various positions relative to the center hole. An alignment peg may be included on the drill guide for insertion into the center hole formed in the glenoid surface to position the plurality of drill guide apertures at predetermined locations in relation to the center hole.

The glenoid component installation instruments of the present invention also include an assembly for reaming the glenoid surface of the scapula to prepare the glenoid surface for receiving the glenoid component. The assembly includes a reamer having a cutting face which is rotatable about an axis of rotation. The cutting face is designed to be rotated in only one predetermined direction for smoothing and preparing the glenoid surface. The reamer assembly also includes ratchet means coupled to the reamer for intermittently rotating the reamer in a predetermined direction about the axis of rotation. The reamer assembly further includes means rotatably coupled to the ratchet means for receiving a pressure force along the axis of rotation to cause the cutting face of the reamer to engage the glenoid surface.

In still another preferred embodiment of the invention, the ratchet means includes a drive member coupled to the reamer for rotating the reamer about its axis of rotation in the predetermined direction and an oscillating member coupled to the drive member for providing intermittent rotational movement to the drive member. The oscillating member includes a handle for alternately rotating the oscillating member in the first predetermined direction and in a second direction opposite the first direction. The handle is aligned at a predetermined angle with respect to the axis rotation.

One feature of the present invention is the provision of a drill guide having a detachable handle and means for coupling the handle to the drill guide in a selected one of a plurality of orientations to align the handle at a selected angle with respect to the drill guide. Advantageously, this feature permits a surgeon to select an angle for attaching the handle which makes positioning the drill guide on the glenoid surface as easy as possible. In addition, the adjustable handle permits a single drill guide to be used for drilling both the left and right side glenoid surfaces. Therefore, the present invention facilitates the formation of holes in the glenoid surface for receiving attachment pegs to secure a glenoid component to the glenoid surface.

Another feature of the present invention is the provision of a reamer assembly including a ratchet drive mechanism for rotating a reamer about its axis of rotation to prepare a surface of a bone for receiving a prosthetic component. Advantageously, the ratchet assembly permits rotation of the reamer against the bone surface despite the limited access available during the normal surgical procedure. The ratchet drive mechanism causes rotation of the reamer in a single direction upon oscillating movement of an oscillating member of the ratchet assembly.

Additional objects, features, and advantageous of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 1 is a perspective view of a glenoid component for replacing a natural glenoid surface of a scapula illustrating the configuration of attachment pegs extending away from a convex surface of the glenoid component;

FIG. 2 is an exploded perspective view of an assembly for aligning and guiding a drill bit illustrating a drill guide separated from a handle for positioning the drill guide on the glenoid surface;

FIG. 3 is an exploded perspective view illustrating the handle connected to the drill guide spaced apart from the glenoid surface and a drill bit for drilling a center hole in the glenoid surface;

FIG. 4 is a sectional view illustrating the position of the drill guide during formation of the center hole in the glenoid surface by the drill bit;

DETAILED DESCRIPTION OF THE DRAWINGS

Figure 6:
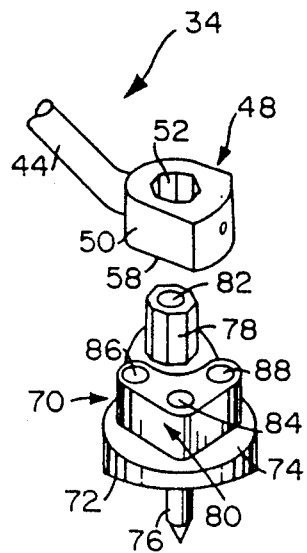
FIG. 6 is an exploded perspective view illustrating a second embodiment of the drill guide for forming a plurality of holes surrounding a center hole in the glenoid surface.

Referring now to the drawings, FIG. 1 illustrates a glenoid component 10 including a body portion 12 having a generally convex surface 14 for abutting a glenoid surface 11 of a scapula 13. Body portion 12 also includes a generally concave surface 16 which provides a bearing surface for a head portion of a humeral component (not shown). Glenoid component 10 includes a center attachment peg 18, a superior attachment peg 20, and an inferior attachment peg 22 extending generally perpendicularly away from convex surface 14. Glenoid component 10 also includes first and second stabilizing pegs 24 and 26, respectively, extending away from convex surface 14. Attachment pegs 18, 20, and 22 and stabilizing pegs 24 and 26 penetrate holes formed in the glenoid surface 11 to secure the glenoid component 10 to the glenoid surface 11.

In order to install glenoid component 10, a plurality of holes must be drilled in glenoid surface 11. The holes must be precisely aligned to receive attachment pegs 18, 20, and 22 and stabilizing pegs 24 and 26 of glenoid component 10.

FIGS. 2-5 illustrate an assembly 30 for guiding a drill bit 54 to form a center hole 55 in glenoid surface 11 for receiving center attachment peg 18. The assembly 30 includes a drill guide 32 and a handle 34. Drill guide 32 includes a generally convex surface 36 for abutting the generally concave glenoid surface 11 and a generally planar outwardly facing second surface 38. A projection 40 extends away from the second surface 38 of drill guide 32. Drill guide 32 is formed to include an aperture 42 extending between first and second surfaces 36 and 38 and through projection 42 to provide a drill guide aperture for drill bit 54.

Handle 34 of assembly 30 includes an elongated rod 44 having a grip portion 46. A head portion 48 is coupled to elongated rod 44. Head portion 48 includes a body portion 50 having a generally planar bottom surface 58. The planar second surface 38 of drill guide 32 provides a support surface for planar bottom surface 58 of head portion 48. Head portion 48 is also formed to include an aperture 52 for coupling head portion 48 to projection 40. Head portion 48 is aligned at an angle A with respect to elongated rod 44 to further facilitate positioning of drill guide 32 on glenoid surface 11. Preferably angle A is about 45°.

Aperture 52 has the same shape as projection 40 so that handle 34 can be coupled to drill guide 32 in one of a plurality of orientations to align handle 34 at a selected angle with respect to drill guide 32 to facilitate positioning of drill guide 32 on glenoid surface 11. A detent 56 is provided in head portion 48 for coupling head portion 48 to projection 40. Projection 40 illustratively has the shape of a right octogonal prism. Therefore, handle 34 can be positioned over the projection 40 in one of eight different orientations to change the angle of handle 34 with respect to drill guide 32. It is understood that projection 40 may have any desired shape to permit handle 34 to be coupled to projection 40 in any number of selected orientations.

FIGS. 3 and 4 illustrate head portion 48 coupled to projection 40 on drill guide 32 in a selected orientation. A surgeon holds grip 46 and moves drill guide 38 into its proper position over glenoid surface 11. By visually inspecting the position of drill guide 32 over glenoid surface 11, the surgeon can align drill guide aperture 42 in substantially the preferred location on glenoid surface 11 to form a center hole 55 in glenoid surface 11.

FIG. 4 illustrates convex surface 36 of drill guide 32 abutting the glenoid surface 11. Drill bit 54 extends through drill guide aperture 42 and bores the center hole 55 in glenoid surface 11. Projection 40 extends a predetermined distance above the second surface 38 of drill guide 32 to provide depth limiting means for engaging a portion 53 of the drill bit 54 to limit the depth that the drill bit 54 penetrates the bone underlying glenoid surface 11.

Figure 5:
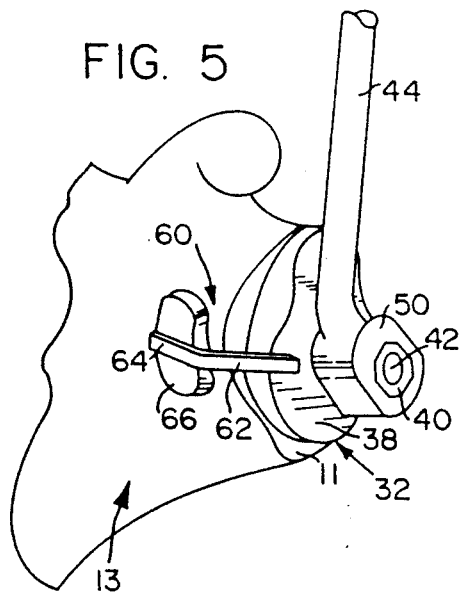
FIG. 5 is a perspective view illustrating an alignment arm which may be used to position the drill guide shown in FIGS. 2-4 in a proper location on the glenoid surface.

FIG. 5 illustrates an optional alignment arm 60 which may be coupled to drill guide 38 for engaging a portion of the glenoid to align drill guide aperture 42 over its predetermined location to drill center hole 55 in glenoid surface 11. The alignment arm 60 includes an L-shaped arm having a first leg 62 coupled to drill guide 38 and a second leg 64 for engaging the glenoid to align drill guide aperture 42 in its predetermined location. A pad portion 66 is coupled to second leg 64 of the L-shaped arm 60. The pad portion 66 engages the glenoid to stabilize the drill guide 32 in its predetermined position. FIG. 5 illustrates the pad 66 contacting the anterior side of the glenoid to center hole 55 along a posterior/anterior axis of the glenoid surface 11.

A second drill guide 70 is provided for forming holes in the glenoid surface 11 surrounding center hole 55 to receive superior attachment peg 20, inferior attachment peg 22, and stabilizing pegs 24 and 26 of glenoid component 10. Drill guide 70 includes a generally convex surface 72 for abutting glenoid surface 11 and a generally planar surface 74 spaced apart from convex surface 72. An alignment peg 76 extends away from convex surface 72 of drill guide 70. Alignment peg 76 is inserted into center hole 55 formed in glenoid surface 11 to position drill guide 70 on glenoid surface 11.

Drill guide 70 includes a projection 78 identical to the projection 40 on first drill guide 32 so that the same handle 34 may be used with both drill guides 32 and 70. Projection 78 is formed to include an aperture 82 which provides a drill guide aperture 82 to form a hole 90 in the glenoid surface 11 for receiving superior attachment peg 20. Head portion 48 of handle 34 is coupled to projection 78 so that the surgeon can align handle 34 in a selected orientation to facilitate positioning and holding drill guide 70 on glenoid surface 11.

Drill guide 70 includes a raised portion 80 formed to include drill guide apertures 84, 86, and 88 for forming holes in glenoid surface 11 for receiving the inferior attachment peg 22, the first stabilizing peg 24, and the second stabilizing peg 26, respectively.

Figure 7:
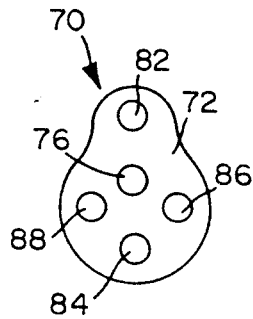
FIG. 7 is a bottom view of the drill guide shown in FIG. 6 illustrating the position of an alignment peg for insertion into the center hole of the glenoid surface for centering the second drill guide.
Figure 8:
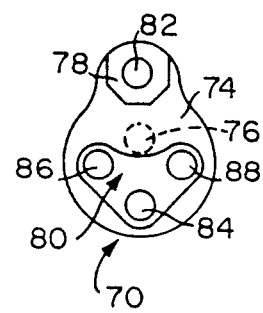
FIG. 8 is a plan view of the drill guide shown in FIG. 6 illustrating the position of the drill guide apertures in relation to the center alignment peg.

FIGS. 7 and 8 illustrate the position of alignment of apertures 82, 84, 86 and 88 on drill guide 70 with respect to alignment peg 76. The spacing of the apertures and 82, 84, 86, and 88 and alignment peg 76 is identical to the spacing of the attachment pegs 18, 20, 22, 24, and 26 on glenoid component 10. It is understood that the spacing and configuration of apertures 82, 84, 86, and 88 may be changed depending upon the configuration of attachment pegs or screw holes on a particular glenoid component.

Figure 9:
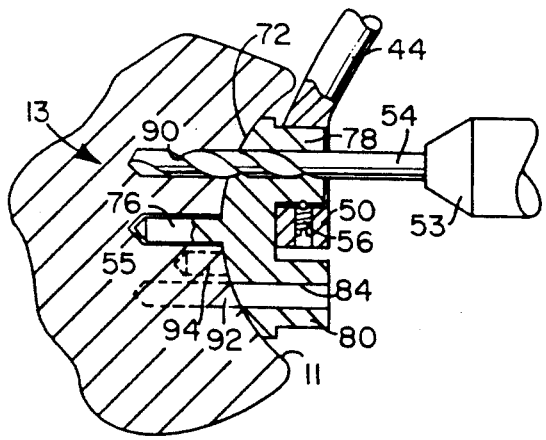
FIG. 9 is a sectional view illustrating the position of the second drill guide and handle on the glenoid surface to guide the drill bit to form additional holes in the glenoid surface.

FIG. 9 illustrates drill guide 70 in its proper position on glenoid surface 11 for forming holes in the glenoid surface. Alignment peg 76 is inserted into center hole 55. Drill bit 54 is shown forming a hole 90 in glenoid surface 11 for receiving superior attachment peg 20 of glenoid component 10. The dotted portions 92 and 94 of FIG. 9 illustrate the position of holes that will subsequently be formed for receiving inferior attachment peg 22 and second stabilizing peg 26, respectively. As with first drill guide 32, handle 34 can be attached to the projection 78 in one of a plurality of orientations to position the handle 34 in the most advantageous position for accessing glenoid surface 11.

Figure 10:
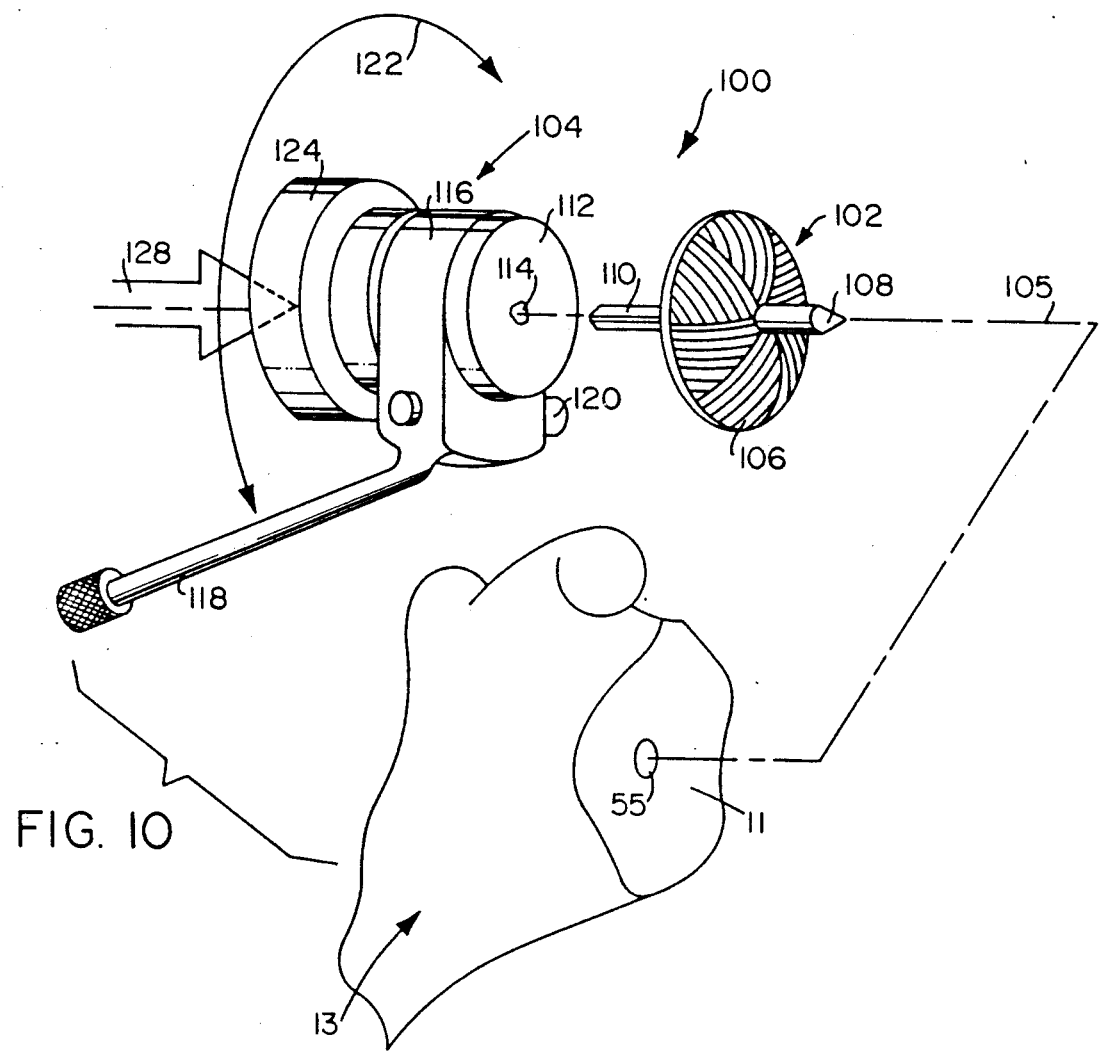
FIG. 10 is an exploded perspective view of a preferred embodiment of a reamer assembly of the present invention illustrating a reamer situated between the glenoid surface and a ratchet drive mechanism.
Figure 11:
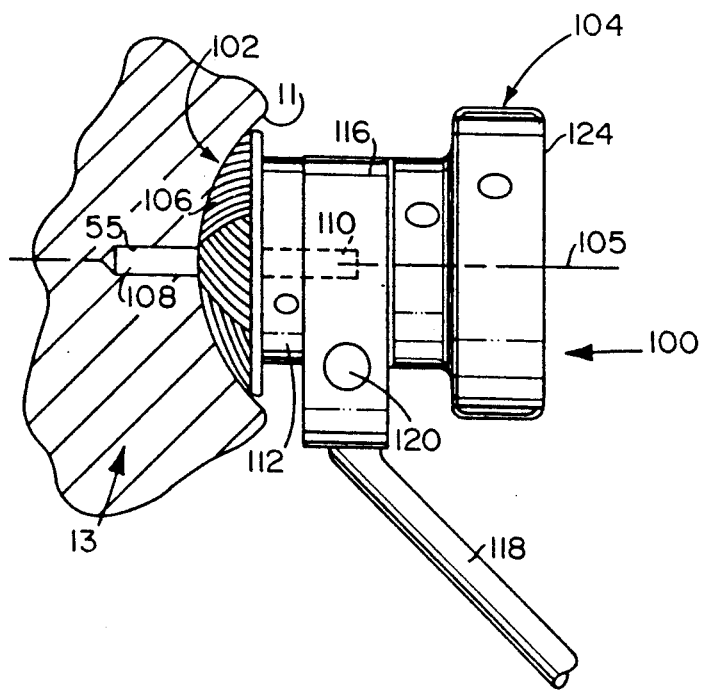
FIG. 11 is a side elevational view of the reamer assembly shown in FIG. 10 illustrating the reamer engaging the glenoid surface.

FIGS. 10 and 11 illustrate a reamer assembly 100 for preparing the glenoid surface 11 to receive glenoid component 10. The reamer assembly 100 includes a reamer 102 and a ratchet assembly 104 for rotating the reamer 102 about its axis of rotation 105 to smooth and prepare glenoid surface 11. Reamer 102 includes a cutting face 106 and an alignment peg 108 for insertion into center hole 55 to align the reamer 102 in a proper orientation on glenoid surface 11. Reamer 102 also includes a boss 110 for insertion into an aperture 114 of ratchet assembly 104 to couple the reamer 102 to the ratchet assembly 104. Cutting face 106 is designed to be rotated in only one direction on glenoid surface 11.

Ratchet assembly 104 includes a drive member 112, an oscillating member 116, and a pressure pad 124. Oscillating member 116 includes a handle 118 to permit an operator to intermittently rotate oscillating member 116 in first and second directions about axis of rotation 105 as illustrated by arrows 122. Oscillating member 116 is coupled to drive member 112 to provide intermittent rotational movement to drive member 112 about axis 105 upon oscillating movement of oscillating member 116.

Oscillating member 116 includes a conventional ratchet mechanism for intermittently engaging drive member 112 to rotate drive member 112 in only a first selected direction while permitting oscillating member 116 to rotate with respect to drive member 112 without engaging and rotating drive member 112 when the oscillating member 116 moves in a second direction opposite the first direction.

An operator applies pressure to rotating bearing surface or pressure pad 124 in the direction of arrow 128 to engage cutting face 106 with glenoid surface 11. Pressure pad 124 is freely rotatable independent of the ratchet action and is used to apply an engaging force along a lateral/medial axis when reamer 102 engages glenoid surface 11.

Ratchet assembly 104 includes a control rod 120 for controlling the direction of rotation of drive member 112 upon oscillating movement of oscillating member 116. By moving control rod 120 between first and second positions, an operator can reverse the direction of rotation of drive member 112. Therefore, the ratchet assembly 104 can be used with reamers 102 designed to be rotated in either direction about axis of rotation 105. Ratchet assembly 104 can also be used to prepare either the left or right side glenoid surfaces.

FIG. 11 illustrates the reamer assembly 100 engaging glenoid surface 11. Alignment peg 108 on reamer 102 is inserted into center hole 55 in glenoid surface 11. An operator moves handle 11B alternately back and forth as shown by arrow 122 in FIG. 10. Movement of handle 118 causes oscillating movement of oscillating member 116 which rotates drive member 112 and reamer 102 in a predetermined direction controlled by the position of control rod 120. Handle 118 is aligned at about a 45° angle with respect to axis of rotation 105 to facilitate rotation of reamer 102. Rotation of cutting face 106 against glenoid surface 11 smoothes and prepares glenoid surface 11 to receive glenoid component 10. Although the reamer assembly 100 is shown for use on a glenoid surface 11, it is understood that the reamer assembly 100 of the present invention can be used to prepare the surface of any bone for receiving a prosthetic component. The ratchet assembly 104 is capable of receiving reamers 102 having different shapes and sizes for use on different bone surfaces.

During the surgical procedure, the surgeon first drills center hole 55 in glenoid surface 11 using drill guide 32 shown in FIGS. 2-5. The surgeon selects an appropriate angle for attaching handle 34 to drill guide 32 to facilitate positioning drill guide 32 on glenoid surface 11. After drill guide 32 is properly positioned on glenoid surface 11, drill bit 54 is used to form center hole 55 and glenoid surface 11. Next, the reamer assembly 100 shown in FIGS. 10 and 11 is used to smooth and prepare glenoid surface 11 for receiving glenoid component 10. Alignment peg 108 is inserted into center hole 55 and reamer 102 is rotated, as discussed above, to smooth and prepare glenoid surface 11. A curved proximal humeral retractor (not shown) may be provided to properly expose the glenoid surface 12 for reaming. The surgeon then forms the holes surrounding the center hole 55 for receiving attachment pegs 20, 22, 24, and 26 of glenoid component 10. The surgeon attaches handle 34 to the second drill guide 70 in a selected position to facilitate positioning of drill guide 70 on glenoid surface 11. Alignment peg 76 is inserted into center hole 55 and the surgeon then rotates drill guide 70 about center hole 55 to position apertures 82, 84, 86, and 88 in their proper positions over glenoid surface 11. The surgeon then holds drill guide 70 in this position and uses drill bit 54 to form holes in the glenoid surface 11 below the drill guide apertures 82, 84, 86, and 88 of drill guide 70. Drill guide 70 is then removed from glenoid surface 11. At this point, glenoid surface 11 is prepared to receive glenoid component 10 to replace the natural socket of the shoulder. Bone cement is inserted into the holes formed in glenoid surface 11 prior to attaching glenoid component 10.

Although the invention has been described in detail with reference to a preferred embodiment, variations and modifications exist within the scope and spirit of the invention as described and defined in the following claims.

What is claimed is:

1. An assembly for aligning and guiding a drill bit to form a hole in a glenoid surface of a scapula at a predetermined location, the assembly comprising a drill guide including a first surface for abutting the glenoid surface and an opposite outwardly facing second surface, the drill guide being formed to include an aperture extending between the first and second surfaces for guiding the drill bit to form the hole in the glenoid surface, a handle for positioning the drill guide on the glenoid surface to align the aperture at the predetermined location over the glenoid surface, and means for selectively coupling the handle to the drill guide in a selected one of a plurality of angled orientations to align the handle at a selected angle with respect to the drill guide to facilitate positioning of the drill guide on the glenoid surface.

2. An assembly for aligning and guiding a drill bit to form a hole in a glenoid surface of a scapula at a predetermined location, the assembly comprising a drill guide including a first surface for abutting the glenoid surface and an opposite outwardly facing second surface, the drill guide being formed to include an aperture extending between the first and second surfaces for guiding the drill bit to form the hole in the glenoid surface, a handle for positioning the drill guide on the glenoid surface to align the aperture at the predetermined location over the glenoid surface, and means for coupling the handle to the drill guide in a selected one of a plurality of orientations to align the handle at a selected angle with respect to the drill guide to facilitate positioning of the drill guide on the glenoid surface, wherein the drill guide includes a projection extending away from the second surface and the coupling means includes a head portion attached to the handle for engaging the projection to position the handle in the selected orientation with respect to the drill guide.

3. The assembly of claim 2, wherein the handle includes an elongated rod attached to the head portion, the head portion being aligned at a predetermined angle with respect to the elongated rod.

4. The assembly of claim 3, wherein the head portion is angled with respect to the elongated rod by about 45 degrees.

5. The assembly of claim 2, wherein the projection is formed to include an aperture to provide the drill guide aperture extending through the projection, the projection extending above the second surface of the drill guide a predetermined distance to provide depth limiting means for engaging a portion of the drill bit to limit the depth that the drill bit penetrates the glenoid surface.

6. The assembly of claim 2, wherein the first surface of the drill guide is generally convex to abut the glenoid surface and the second surface is generally planar to provide a support surface for the head portion.

7. The assembly of claim 2, wherein the projection includes a plurality of side faces oriented substantially perpendicularly to the second surface and the head portion is formed to include means for engaging the plurality of side faces to permit the head portion to be coupled to the projection to align the handle in one of the plurality of orientations.

8. The assembly of claim 7, wherein the projection includes at least five side faces.

9. The assembly of claim 2, wherein the projection includes an outer surface having a polygonal cross section and the head portion includes means for engaging the outer surface of the projection to permit the head portion to be attached to the projection in one of the plurality of orientations.

10. The assembly of claim 9, wherein the projection has the shape of a right octogonal prism.

11. An assembly for aligning and guiding a drill bit to form a hole in a glenoid surface of a scapula at a predetermined location, the assembly comprising
a drill guide including a first surface for abutting the glenoid surface and an opposite outwardly facing second surface, the drill guide being formed to include an aperture extending between the first and second surfaces for guiding the drill bit to form the hole in the glenoid surface,
a handle for positioning the drill guide on the glenoid surface to align the aperture at the predetermined location over the glenoid surface, and
means for coupling the handle to the drill guide in a selected one of a plurality of orientations to align the handle at a selected angle with respect to the drill guide to facilitate positioning of the drill guide on the glenoid surface, further comprising alignment means coupled to the drill guide for engaging a portion of a scapula to facilitate positioning of the drill guide aperture over the predetermined location on the glenoid surface.

12. The assembly of claim 11, wherein the alignment means includes a L-shaped arm having a first leg coupled to the drill guide and a second leg for engaging the scapula to align the drill guide aperture in its predetermined location.

13. The assembly of claim 12, wherein the alignment means further includes a pad portion coupled to the second leg of the L-shaped arm, the pad portion engaging the scapula to stabilize the drill guide on the glenoid surface.

14. An assembly for aligning and guiding a drill bit to form a plurality of holes in a glenoid surface of a scapula at predetermined locations in relation to a center hole formed in the glenoid surface, and assembly comprising
a drill guide including an alignment peg for insertion into the center hole formed in the glenoid surface, the drill guide being formed to include a plurality of apertures for guiding the drill bit to form the plurality of holes in the glenoid surface,
a handle for positioning the drill guide on the glenoid surface to align the plurality of apertures formed in the drill guide at their respective predetermined locations over the glenoid surface, and
means for coupling the handle to the drill guide in a selected one of a plurality of orientations to align the handle at a selected angle with respect to the drill guide to facilitate positioning of the drill guide on the glenoid surface.

15. The assembly of claim 14, wherein the drill guide includes a first surface for abutting the glenoid surface, a second surface spaced apart from the first surface, and a projection extending away from the second surface of the drill guide, the coupling means including a head portion attached to the handle for engaging the projection to position the handle in the selected orientation with respect to the drill guide.

16. The assembly of claim 15, wherein the projection is formed to include an aperture to provide a drill guide hole extending through the projection, the projection extending above the second surface of the drill guide by a predetermined distance to provide depth limiting means for engaging a portion of the drill bit to limit the depth that the drill bit penetrates the glenoid surface.

17. The assembly of claim 15, wherein the first surface of the drill guide is generally convex to abut the glenoid surface, the alignment peg extending away from the first surface for insertion into the center hole formed in the glenoid surface, and the second surface is generally planar to provide a support surface for the head portion.

18. The assembly of claim 15, wherein the projection includes a plurality of side faces oriented substantially perpendicularly to the second surface and the head portion is formed to include means for engaging the plurality of side faces to permit the head portion to be coupled to the projection in various selected positions to align the handle in one of the plurality of orientations.

19. The assembly of claim 15, wherein the projection includes an outer surface having a polygonal cross section and the head portion includes means for engaging the outer surface of the projection to permit the head portion to be attached to the projection in various selected positions to align the handle in one of the plurality of orientations.

20. The assembly of claim 19, wherein the projection has the shape of a right octogonal prism.

21. The assembly of claim 14, wherein the drill guide is formed to include a superior aperture and an inferior aperture for guiding the drill bit to form a superior hole and an inferior hole on the glenoid surface aligned with the center hole to lie along a superior/inferior axis of the glenoid surface.

22. The assembly of claim 21, wherein the drill guide is formed to include an anterior aperture and a posterior aperture spaced apart from the superior/inferior axis in opposite directions for guiding the drill bit to form an anterior hole and a posterior hole, respectively, in the glenoid surface along an anterior/posterior axis of the glenoid surface.

23. An assembly for reaming a surface of a bone, the assembly comprising
a reamer including a cutting face, the reamer being rotatable about an axis of rotation,
means coupled to the reamer for rotating the reamer in a predetermined direction about the axis of rotation, and
means rotatably coupled to the rotating means and independently rotatable relative to said rotating means rotation to cause the cutting face of the reamer to engage the surface of the bone.

24. The assembly of claim 23, wherein the rotating means includes ratchet means having a one way drive means coupled to the reamer for rotating the reamer about its axis of rotation in the predetermined direction and an oscillating member coupled to the one way drive means for transmitting intermittent rotational movement to the one way drive means.

25. The assembly of claim 24, wherein the oscillating member is formed to include a handle for alternately rotating the oscillating member in the first direction and in a second direction opposite the first direction, the handle being aligned at a predetermined angle with respect to the axis of roation.

26. An assembly for reaming a surface of a bone, the assembly comprising
a reamer including cutting face, the reamer being rotatable about an axis of rotation,
a drive means coupled to the reamer for rotating the reamer about its axis of rotation in a first direction,
an oscillating member coupled to the drive means for transmitting intermittent rotational movement to the drive means about the axis of rotation, the oscillating member including means for permitting rotation of the oscillating member alternately in the first direction and in a second direction opposite the first direction and ratchet means driven by the oscillating member for intermittently engaging the drive means to rotate the drive means in only the first direction upon rotation of the oscillating member in the first direction while permitting the oscillating member to rotate with respect to the drive means without engaging and rotating the drive means when the oscillating member moves in a second direction, and a pressure pad rotatably coupled to the oscillating member to permit an operator to apply pressure along the axis of rotation of the reamer to cause the cutting face of the reamer to engage the surface of the bone.

27. The assembly of claim 26, wherein the reamer includes an alignment post positioned along its axis of rotation for engaging a hole formed in the bone to position the reamer in a predetermined location on the surface of the bone.

28. The assembly of claim 26, wherein the oscillating member is formed to include a handle for alternately rotating the oscillating member about the axis of rotation in the first and second directions.

29. The assembly of claim 28, wherein the handle is angled by about 45 degrees with respect to the axis of rotation of the reamer.

30. The assembly of claim 26, wherein the oscillating member includes means for controlling the direction of rotation of the drive means, the controlling means being reversible so that the direction of rotation of the drive means can be changed.

* * * * *